United States Patent
Nishikaze

(10) Patent No.: US 11,906,522 B2
(45) Date of Patent: Feb. 20, 2024

(54) GLYCAN ANALYSIS METHOD

(71) Applicant: SHIMADZU CORPORATION, Kyoto (JP)

(72) Inventor: Takashi Nishikaze, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 93 days.

(21) Appl. No.: 16/347,639

(22) PCT Filed: Nov. 7, 2016

(86) PCT No.: PCT/JP2016/082909
§ 371 (c)(1),
(2) Date: May 6, 2019

(87) PCT Pub. No.: WO2018/083790
PCT Pub. Date: May 11, 2018

(65) Prior Publication Data
US 2019/0317101 A1 Oct. 17, 2019

(51) Int. Cl.
*G01N 33/58* (2006.01)
*H01J 49/00* (2006.01)

(52) U.S. Cl.
CPC ............ *G01N 33/58* (2013.01); *H01J 49/004* (2013.01); *H01J 49/0027* (2013.01); *G01N 2400/10* (2013.01)

(58) Field of Classification Search
None
See application file for complete search history.

(56) References Cited

U.S. PATENT DOCUMENTS

2011/0089033 A1 4/2011 Shimaoka et al.
2014/0178912 A1* 6/2014 Liu .................. B01J 43/00
435/18

FOREIGN PATENT DOCUMENTS

JP 2013-205221 A 10/2013
WO 2009/150834 A1 12/2009

OTHER PUBLICATIONS

PubChem, Benzocaine, retrieved from internet site : https://pubchem.ncbi.nlm.nih.gov/compound/Benzocaine#section=Stability-Shelf-Life the pKa data is from 1965 source. (Year: 1965).*
Erika Lattová et al., "Influence of the Labeling Group on Ionization and Fragmentation of Carbohydrates in Mass Spectrometry", American Society for Mass Spectrometry, 2005, vol. 16, pp. 683-696 (total 14 pages).

(Continued)

*Primary Examiner* — Xiaoyun R Xu
(74) *Attorney, Agent, or Firm* — Sughrue Mion, PLLC

(57) ABSTRACT

Glycans having a branched structure are labeled with a labeling agent, such as 2-aminobenzoic acid, having one site that is easily negatively charged. At this time, reduction which is usually performed in labeling by reduction amination is not performed. A sample for mass spectrometry containing the labeled form of glycans thus obtained is prepared, and is subjected to MS/MS analysis in negative ion mode. In the MS/MS spectra obtained by the MS/MS analysis, peaks of E ions, D ions and the like which reflect the branched structure clearly appear. As a result, structural analysis of an entirety of the glycan including the branched structure can be easily performed.

9 Claims, 5 Drawing Sheets

(56) References Cited

OTHER PUBLICATIONS

Joseph Zaia et al., "Tandem Mass Spectrometric Strategies for Determination of Sulfation Positions and Uronic Acid Epimerization in Chondroitin Sulfate Oligosaccharides", American Society for Mass Spectrometry, 2003, vol. 14, pp. 1270-1281 (total 12 pages).
Hsing Ling Cheng et al., "Determination of Linkages of Linear and Branched Oligosaccharides Using Closed-Ring Chromophore Labeling and Negative Ion Trap Mass Spectrometry", American Society for Mass Spectrometry, 2002, vol. 13, pp. 1322-1330 (total 9 pages).
Communication dated Oct. 24, 2019 from European Patent Office in counterpart EP Application No. 16920740.4.
Takashi Nishikaze et al., "Sensitive Analyses of Neutral N-Glycans using Anion-Doped Liquid Matrix $G_3CA$ by Negative-Ion Matrix-Assisted Laser Desorption/Ionization Mass Spectrometry", Analytical Chemistry, 2012, pp. 6097-6103, vol. 84 No. 12.
David Harvey, "Collision-induced fragmentation of negative ions from N-linked glycans derivatized with 2-aminobenzoic acid", Journal of Mass Spectrometry, 2005, pp. 642-653, vol. 40.
Takashi Nishikaze et al., "Structural Analysis of N-Glycans by the Glycan-Labeling Method Using 3-Aminoquinoline-Based Liquid Matrix in Negative-Ion MALDI-MS", Analytical Chemistry, 2012, pp. 9453-9461, vol. 84.
Shu-Ting Chen et al., "Linkage and Branch Analysis of High-Mannose Oligosaccharides Using Closed-Ring Labeling of 8-Aminopyrene-1,3,6-Trisulfonate and P-Aminobenzoic Ethyl Ester and Negative ion Trap Mass Spectrometry", Journal American Society for Mass Spectrometry, Aug. 2012, pp. 1408-1418, vol. 23, Issue 8.
Hsing-Ling Cheng et al., "Linkage and Branch Determination of N-linked Oligosaccharides Using Sequential Degradation/Closed-Ring Chromophore Labeling/Negative Ion Trap Mass Spectrometry", Journal American Society for Mass Spectrometry, 2007, pp. 248-259, vol. 18, No. 2.
International Search Report for PCT/JP2016/082909 dated Nov. 29, 2016 [PCT/ISA210].
Written Opinion for PCT/JP2016/082909 dated Nov. 29, 2016 [PCT/ISA237].
Second Office Action dated Jan. 13, 2022 from the China National Intellectual Property Administration in CN Application No. 201680090635.2.
Communication dated Jun. 21, 2022 from the State Intellectual Property Office of P.R. of China in Application No. 201680090635.2.
Notice of Allowance dated Oct. 8, 2022 issued by the Chinese Patent Office in Chinese Application No. 201680090635.2.

* cited by examiner

GLYCAN ANALYSIS METHOD

CROSS REFERENCE TO RELATED APPLICATIONS

This application is a National Stage of International Application No. PCT/JP2016/082909 filed Nov. 7, 2016.

TECHNICAL FIELD

The present invention relates to a method for analyzing a structure of glycan using mass spectrometry, and in particular to a method useful for structural analysis of glycan having a branched structure also referred to as a tree-like structure)

BACKGROUND ART

It is said that more than half of proteins constituting a living body are subject to glycosylation, and glycosylation plays an important role in regulating structure and function of proteins. Recent studies also show that a glycan expressed on a cell surface is involved in various in vivo phenomena such as intercellular interaction, signal transduction, development/differentiation, fertilization, and cancer metastasis.

Glycans that modify proteins rarely have a structure in which monosaccharides are connected in a linear chain, and in many cases they have a branched structure. The structure of such glycans having a branched structure is extremely versatile, and the structure exerts a large influence on the function of the protein. Therefore, structural analysis of glycans is important in various fields such as physiology, life science, and medicine.

In recent years, mass spectrometry is widely used for structural analysis of glycans, especially that accompanied by ion dissociation operation called tandem mass spectrometry, multistage mass spectrometry ($MS^n$), or the like. Glycan structural analysis using mass spectrometry is generally performed based on mass spectra (in this specification, MS/MS spectra obtained by MS/MS analysis may also be referred to as mass spectra) acquired under positive ion mode. However, dissociation of positively ionized glycan by collision induced dissociation (CID) method often causes dissociation at a glycosyl bond between monosaccharides, making it difficult to obtain information on branched structure. Therefore, although such a method is useful for estimating monosaccharides constituting glycan, it is not so suitable for structural analysis of glycans having a branched structure.

On the other hand, glycan structural analysis based on mass spectra acquired under negative ion mode has been also attempted, though it is not so common. It is known that dissociation reflecting a branched structure tends to occur specifically when negatively ionized glycan are dissociated by CID. For example, in N-linked glycans, D ions which reflect structural information of 1-6 arms of two branches and E ions which reflect structural information of 1-3 arms are likely to be generated, and it is possible to estimate a branched structure by detecting these ions. Moreover, these product ions are considered to be generated by simple primary dissociation, and the structural information of an original molecule is likely to be reflected in the product ions compared with ions generated by complicated secondary dissociation or tertiary dissociation. Therefore, there is an advantage that, for example, when a specific product ion is observed on mass spectra, a diagnostic analysis can be performed in which a partial structure of the original molecule is uniquely determined. From this, it can be said that mass spectrometry in negative ion mode is advantageous for structural analysis of glycans having a branched structure.

However, there is a problem that glycans are hardly negatively ionized. Since sialic acid, one of monosaccharides, has a carboxyl group, it is easily charged to a negative charge. Therefore, an acidic glycan containing sialic acid relatively easily become a negative ion. In actual measurement, however, derivatization is often performed by preprocessing so as to neutralize a negative charge of a sialic acid moiety in order to prevent a loss of sialic acid. Therefore, in general, even when a glycan contains sialic acid, it is necessary to negatively ionize a neutral glycan having no functional group to be substantially deprotonated.

As one method for negatively ionizing neutral glycans, a method of negative ionization by adding anions to glycan molecules has been developed. For example, Patent Literature 1 and Non Patent Literature 1 each disclose, in order to negatively ionize glycans that are substantially neutral by a matrix-assisted laser desorption ionization (MALDI) method, a method for preparing a sample for measurement by adding anions to a special liquid matrix. The liquid matrix is an ionic liquid composed of, for example, ions of an amine and ions of an acid group-containing organic substance such as p-coumaric acid, and the anion is tetrafluoroboric acid or the like. However, with such methods, the type of matrices that can be used is considerably restricted, and it is not possible to use a general MALDI matrix, which is inexpensive and easily available. In addition, such a special matrix may not be suitable depending on the type of mass spectrometer. For example, a liquid matrix sometimes causes reduction in resolution due to the thickness of the matrix itself or other influences in a usual matrix-assisted laser desorption ionization time-of-flight mass spectrometer (MALDI-TOFMS). Therefore, it is preferable to use it in a mass spectrometer in which an ion trap described later is provided in a front stage of TOFMS. Also, even when the type of anion to be added is the same, product ions may not be obtained at all, depending on the type of glycan, so that it is difficult to select an anion. Furthermore, there is also a problem that a covalent bond is formed between anions added to glycans and the glycans, so that diagnostic product ions useful for structural analysis may not be obtained.

In some cases, structural analysis of glycans may be performed in a state where the glycans are released from glycoproteins, glycopeptides or the like. But it is often performed in a state where reducing terminals of the glycans are labeled. Well-known method is labeling for fluorescent labeling. Some labeling agents have a moiety that is easily negatively charged, and When glycans are labeled with such a labeling agent, negative ionization of glycans becomes easy. This can he applied irrespective of the type of glycan such as neutral glycan, sialyl glycan, and modified sialyl glycan, and the glycans can be negatively ionized efficiently.

However, according to the report of Non Patent Literature 2, MS/MS spectra obtained by MS/MS analysis of glycans labeled with a labeling agent that is easily negatively charged in negative ion mode are not specific against expectations. Only a plurality of product ions called y series, in which glycosyl bonds between monosaccharides are cleaved, is observed. In Non Patent Literature 2, it is concluded that, even when reducing terminals of glycans are labeled with a labeling agent that is easily negatively charged and subjected to MS/MS analysis in the negative ion mode, a product ion reflecting a branched structure which is important for the structural analysis of glycans cannot be obtained.

Thus, in order to perform glycan structural analysis by mass spectrometry in negative ion mode, regardless of whether the glycans are labeled, as described above, there is no way other than adopting a method of preparing a sample for MALDI using a special matrix added with anions, and measuring with a special mass spectrometer.

CITATION LIST

Patent Literature

Patent Literature 1: JP 2013-205221 A

Non Patent Literature

Non Patent Literature 1: T. Nishikaze and 3 others, "Sensitive Analysis of Neutral N-Glycans using Anion-Doped Liquid Matrix G3CA by Negative-Ion Matrix-Assisted Laser Desorption/Ionization Mass Spectrometry", Anal. Chem., 2012, Vol. 84, No. 12, pp. 6097-6103

Non Patent Literature 2: D. J. Harvey, "Collision-induced fragmentation of negative ions from N-linked glycans derivatized with 2-aminobenzoic acid", Journal of Mass Spectrometry, 2005, Vol. 40, pp. 642-653

Non Patent Literature 3: T. Nishikaze and 3 others, "Structural analysis of N-glycans by the glycan-labeling method using 3-aminoquinoline-based liquid matrix in negative ion MALDI-MS", Anal. Chem., 2012, Vol. 84, No. 12, pp. 6097-6103

Non Patent Literature 4: Chen S T. and 1 other, "Linkage and Branch Analysis of High-Mannose Oligosaccharides Using Closed-Ring Labeling of 8-Aminopyrene-1,3,6-Trisulfonate and P-Aminobenzoic Ethyl Ester and Negative Ion Trap Mass Spectrometry", Journal of The American Society for Mass Spectrometry, August 2012, Vol. 23, Issue 8, pp. 1408-1418

SUMMARY OF INVENTION

Technical Problem

As described above, in the conventional glycan analysis method, there has been a problem that the preprocessing for preparing samples requires a large cost and complicated operations, such as requiring an expensive special matrix, instead of an easily available general matrix, in order to certainly negatively ionize glycans to be analyzed to acquire MS/MS spectra reflecting the branched structural information. Furthermore, there are cases where the type of usable mass spectrometer is limited, which is not a general-purpose method.

The present invention has been made in view of these problems, and it is an object of the present invention to provide a glycan analysis method, when performing glycan structural analysis using mass spectrometry, which is capable of certainly negatively ionizing glycans by low-cost simple preprocessing, and acquiring MS/MS spectra reflecting branched structural information of the glycans.

Solution to Problem

Generally, a method called reduction amination (or reductive amination) is often used for labeling glycans. This is a method of reacting reducing terminals of glycans with a labeling agent having an amino group and then causing a reduction reaction with a reducing agent, thereby stabilizing a labeled form. For example, a labeling method used in Non Patent Literature 2 is also a reduction amination method.

So far, the present inventor has attempted glycan structural analysis by negative ion mode on glycans labeled using a basic or neutral labeling agent by methods described in Patent Literature 1 and Non Patent Literature 1, and reported the results in Non Patent Literature 3 and the like. The present inventor has confirmed in its experiment that the presence or absence of a reduction process to obtain a stable labeled product affects whether MS/MS spectra useful for glycan structural analysis are obtained. Then, it has come to a conclusion that it is preferable not to perform reduction in order to obtain diagnostic product ion information, almost regardless of whether labeling is performed and the type of labeling. This phenomenon is presumed to be attributed to the fact that an N-acetylglucosamine residue at a base (reducing terminal side) of the glycan is completely opened by reduction after labeling, and as a result, electron transfer within a ring at the time of CID becomes difficult and secondary dissociation and tertiary dissociation are promoted.

In addition, Non Patent Literature 4 has reported an experimental example in which a labeling method without reduction is applied to glycans. Here, it is considered that labeling without reduction (referred to as "closed-ring labeling" in Non Patent Literature 4) is performed using neutral 4-aminobenzoic acid ethyl ester (ABEE) as a labeling agent, and MS/MS analysis is performed in negative ion mode, whereby mass spectra equivalent to those of underivatized glycans can be obtained. On the other hand, an experiment of performing labeling without reduction using acidic 8-aminopyrene-1,3,6-trisulfonic acid (APTS) as a labeling agent has also been done, and it is considered that specific product ions could not be observed, unlike the case of using a neutral labeling agent. That is, in this report, from the viewpoint of acquiring useful information for analyzing a branched structure, it has been concluded that there is an effect of not performing reduction when using a neutral labeling agent, but there is no effect of not performing reduction when using an acidic labeling agent.

However, in consideration of the results in the case of using a basic or neutral labeling agent, the present inventor has intensively studied by experiments and the like based on supposition that the presence or absence of reduction will affect a mode of dissociation also when labeling with a labeling agent that is easily negatively charged, that is, an acidic labeling agent. As a result, the present inventor has found that it is possible to efficiently obtain a deprotonated form by performing mass spectrometry in negative ion mode after labeling glycans using an acidic labeling agent that is easily negatively charged without performing reduction. Furthermore, the present inventor has also found that branched structure-specific product ions can be observed by performing MS/MS analysis including CID targeting the deprotonated form, and has completed the present invention.

That is, the present invention made to solve the above problems is a method for analyzing a structure of glycan using mass spectrometry, the method including:

a) a sample preparation step of preparing a sample by labeling glycan to be analyzed without reduction, using a labeling agent having at least one site capable of stably presenting a negative charge in a molecule; and b) an analysis execution step of subjecting the sample to MS/MS analysis in negative ion mode, wherein branched structural information of the glycan is acquired from a result of MS/MS analysis.

In the glycan analysis method according to the present invention, one of the following two methods can typically be adopted as a method for performing labeling without reduction.

(1) As described above, a general method used for labeling glycans is reduction amination, in which case a labeling agent and a reducing agent are used in combination. In general, when a substance derived from a labeling agent binds to a free reducing terminal of a partial structure near a binding portion is reduced by an action of the reducing agent, and a stable labeled form is formed. In this case, labeling without reduction can be performed by not using a reducing agent.

(2) As a labeling agent often used for labeling proteins, there are N-hydroxysuccinimide (NHS) esters that bind to an amino group, and in recent years, a labeling agent for glycans using them has also been commercially available. Unlike labeling agents by reduction amination, such labeling agents originally do not need to be reduced at the time of labeling. Even such a labeling agent of NHS esters can be used in the glycan analysis method according to the present invention as long as it has at least one site capable of stably presenting a negative charge. In this case, labeling itself is labeling without reduction as described above.

In the glycan analysis method according to the present invention, in the sample preparation step, a sample containing a labeled form of non-reduced glycans as a sample is prepared. For example, in performing mass spectrometry using a MALDI mass spectrometer, a liquid matrix is used as a matrix, and a substance serving as a labeling agent is used as an acid group-containing organic substance constituting the liquid matrix. As a result, as part of the work of preparing a sample for MALDI mass spectrometry, it is possible to perform labeling of glycans without reduction and simplify a working process. In the analysis execution step, the prepared sample is subjected to MS/MS analysis using an appropriate mass spectrometer. In the MS/SIS spectra obtained by the MS/MS analysis, for example, D ions, E ions, and the like which reflect a branched structure of glycans are observed as product ions. By utilizing such product ion information, it is possible to estimate the structure of glycans having a branched structure.

In the glycan analysis method according to the present invention, the site capable of stably presenting a negative charge in a labeling agent generally refers to a functional group having a property that is easily negatively charged such as a carboxyl group, a phosphoric acid group, or a sulfate group. Examples of typical labeling agents having one carboxyl group include 2-aminobenzoic acid (2AA), 5-aminosalicylic acid (5ASA), and the like. Also, examples of a compound having a sulfate group and usable as a labeling agent include 2-aminobenzenesulfonic acid, 2-amino-1-naphthalenesulfonic acid, and the like. Examples of a compound having a phosphoric acid group and usable as a labeling agent include 4-aminobenzylphosphonic acid, and the like.

On the other hand, as labeling agents having one carboxyl group in the above-described NHS esters, there are "79636 Sigma Atto 590 NHS ester" (molecular formula: $C_{41}H_{42}ClN_3O_{11}$), "72464 Sigma Atto 565 NHS ester" (molecular formula: $C_{35}H_{34}ClN_3O_{11}$), and "F9551 Sigma-Aldrich" (fluoroscein 5-carboxymethyl thiopropanoic acid NHS ester), and the like all manufactured by SIGMA-ARDRICH, USA. Also, as labeling agents having one sulfate group in the same NHS esters, there are "73494 Sigma Dy-560 NHS ester" (molecular formula: $C_{37}N_{44}N_4O_{10}S_2$), "55536 Sigma Fluorescent Red Mega 480 NHS ester" (molecular formula: $C_{30}H_{33}N_3O_9S$), and the like.

Generally known labeling agents for glycans include those having one site that stably presents a negative charge in a molecule and those having a plurality of sites. For example, the APTS utilized in the experiment reported in the Non Patent Literature 4 has three sulfate groups and is strongly acidic. According to such conventional knowledge, when there is a plurality of sites that stably present a negative charge in a molecule, product ions which reflect a branched structure may not be observed. Therefore, in the glycan analysis method according to the present invention, it is preferable to use, as the labeling agent, one having only one site that stably presents a negative charge in a molecule.

Also, the labeling agent preferably has an amino group, a hydrazide group, an aminooxy group, or a corresponding basic functional group, and binds to a reducing terminal of the glycan. Another type of labeling agent preferably reacts with an amino group of a glycosylamine structure in the glycan. The above-described 2AA, 5ASA, and the like are compounds satisfying these conditions.

Moreover, in the glycan analysis method according to the present invention, the analysis execution step preferably executes MS/MS analysis using a deprotonated form of the glycan as a precursor ion.

The glycans to be analyzed in the glycan analysis method according to the present invention are, for example, glycans contained in glycoproteins or glycopeptides, that is, glycans that modify proteins, peptides, or the like. In analyzing the structure of such glycans, a preprocessing step of cutting out (releasing) glycans from glycoproteins, glycopeptides, and the like is usually necessary, and labeling is performed on the glycans thus obtained.

Furthermore, in the glycan analysis method according to the present invention, mass spectrometry is typically MALDI mass spectrometry which performs ionization by MALDI method, but an ionization method is not limited to the MALDI method as long as it is an ionization method capable of generating ions which are deprotonated forms. Specific examples of other useful ionization methods include electrospray ionization (ESI) method, and the like. In the case of the ESI method, multiply charged ions other than single deprotonated form are also produced, so that MS/MS analysis may be performed using the multiply charged ions (multiply deprotonated forms) as precursor ions. As a matter of course, mass spectrometry may be performed while performing component separation on a column, using an LC-MS system in which a high performance liquid chromatograph (HPLC) and such a mass spectrometer are connected.

ADVANTAGEOUS EFFECTS OF INVENTION

According to the glycan analysis method according to the present invention, glycans having a branched structure are certainly negatively ionized while a sample is prepared by a general preprocessing instead of a complicated and costly preprocessing, and MS/MS spectra reflecting the branched structural information can be acquired. Specifically, for example, in performing MALDI mass spectrometry, a sample may be prepared using a general matrix, that is, an inexpensive and easily available matrix for MALDI mass spectrometry. As a result, it is possible to estimate the structure of glycans having a branched structure relatively simply and at low cost.

DESCRIPTION OF EMBODIMENTS

Figure 1:
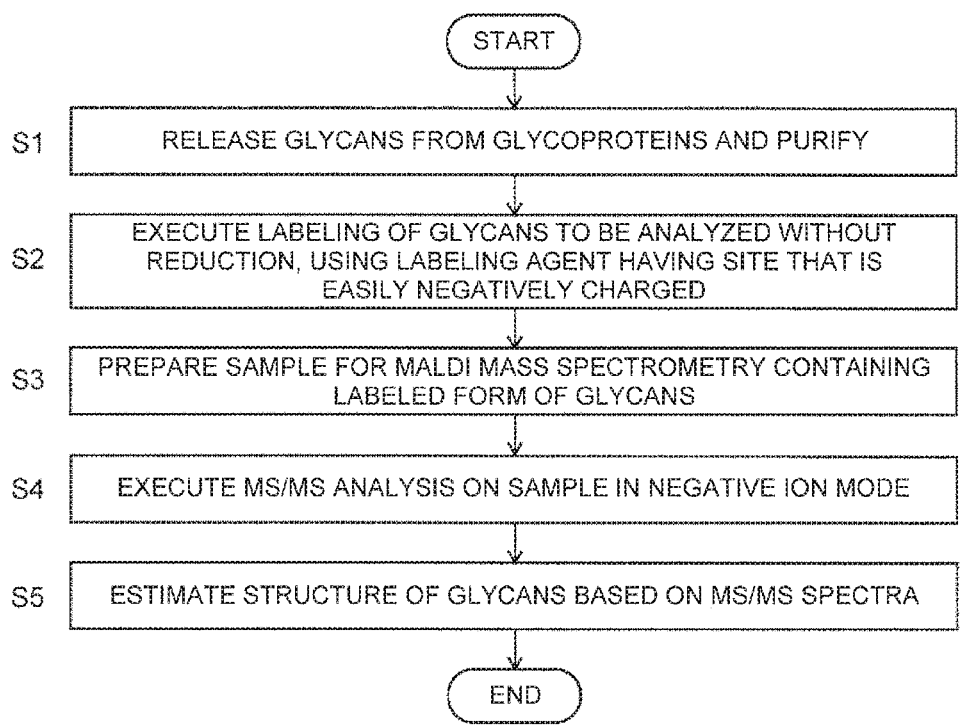
FIG. 1 is a schematic flowchart of an analysis procedure in a glycan analysis method according to an embodiment of the present invention.

First, an analysis procedure in a glycan analysis method according to an embodiment of the present invention will be described with reference to FIG. 1. FIG. 1 is a schematic flow chart of this analysis procedure. Here, a case where a structure of glycans that modify proteins is analyzed using a MALDI mass spectrometer as a mass spectrometer will be exemplified.

First, glycans are released from glycoproteins containing glycans to be analyzed by a known method, and the released glycans are further purified to prepare a sample (step S1).

Next, the glycans to be analyzed are labeled using, as a labeling agent, an appropriate compound containing a site that is easily negatively charged. The site that is easily negatively charged is typically a functional group that is easily negatively charged, that is, easily deprotonated, such as a carboxyl group, a phosphate group, or a sulfate group. The important thing here is to perform labeling without reduction (step S2).

Generally known labeling agents for glycans often perform labeling by reduction amination, but such labeling agents are used in combination with a reducing agent. That is, by reacting the glycan with the labeling agent, a compound derived from the labeling agent is bound to the free reducing terminal of the glycan. Subsequently, a part of the compound bound to the glycan is reduced by the action of the reducing agent, and stable labeled glycan is formed. On the other hand, in using a labeling agent that performs labeling by reduction amination in the glycan analysis method according to this embodiment, occurrence of a reduction reaction is prevented without using a reducing agent.

The above-described 2AA and 5ASA are labeling agents which contain one carboxyl group and an amino group and bind to the reducing terminal that is a ring opening of the glycan, and are suitable for labeling that does not use a reducing agent as described above.

On the other hand, since an NHS ester known as a labeling agent for proteins is a compound binding to an amino group, it can also bind to the amino group of glycosylamine in the glycan. That is, NHS esters can be used as labeling agents for glycans immediately after being released from glycoproteins by an enzyme such as PNGase F (i.e., glycans having a glycosylamine structure). There are various labeling agents of NHS esters, some of which contain the above-described functional group that is easily negatively charged, and they can also be used as labeling agents for negatively ionizing glycans. Labeling using NHS esters is different from the above-described labeling by reduction amination in a mechanism of reaction, and there is no need to perform reduction. Therefore, in labeling glycans using NHS esters, labeling itself is labeling without reduction.

The above-described "79636 Sigma Atto 590 NHS ester", "72464 Sigma Atto 565 NHS ester", "F9551 Sigma-Aldrich", and the like have one carboxyl group, and "73494 Sigma Dy-560 NHS ester", "55536 Sigma Fluorescent Red Mega 480 NHS ester", and the like have one sulfate group. They are suitable for labeling without reduction described above.

Next, a sample for MALDI mass spectrometry is prepared, using a labeled form of glycans formed by labeling without reduction as described above as a sample and using an appropriate matrix (step S3). As will be described later, in a case where a liquid matrix is used for sample preparation and the labeling agent mentioned in step S2 is available as an acid group-containing organic substance constituting the liquid matrix, the labeling without reduction and the preparation of the sample for MALDI mass spectrometry can be performed substantially in parallel or continuously.

Then, the sample prepared in step S3 is subjected to MS/MS analysis in negative ion mode, using a mass spectrometer equipped with a MALDI ion source and capable of MS/MS analysis (step S4). In MS/MS analysis, deprotonated ions of the labeled glycans may be used as precursor ions.

In the MS/MS spectra obtained for the glycans labeled as described above, peaks derived from product ions reflecting the branched structure of glycans, for example, D ions and E ions, clearly appear. Also, when N-acetylglucosamine is present on the reducing terminal side of the glycan, a peak derived from ions due to ring dissociation of its N-acetylglucosamine residue also appears. Therefore, such product ions reflecting the branched structure are detected, and the structure of glycans is estimated based on, for example, a mass-to-charge ratio of the product ions (step S5).

As described above, the glycan analysis method according to this embodiment can accurately estimate a structure of glycans having a branched structure.

EXAMPLES

Hereinafter, experimental examples conducted based on the procedure of the glycan analysis method according to the foregoing embodiment and comparative examples conducted based on a procedure of a conventional glycan analysis method performed for comparison with the experimental examples will be specifically described.

Comparative Example 1

As a sample, 2-AA labeled NA2 glycan manufactured by Ludger Ltd, UK was used. It has a structure in which 2AA binds to a reducing terminal of NA2 glycan with a biantennary structure described in the following chemical formula, and reduction treatment is performed after labeling.

[Chemical formula 1]

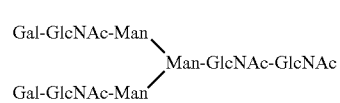

The 2-AA labeled glycans were dissolved in ultrapure water to a concentration of 1 pmol/uL, 1 uL of the solution was collected, and dropped to a MALDI sample plate (μFocus MALDI plate manufactured by Hudson Surface Technology, USA). Then, 2,5-dihydroxybenzoic acid (DHB) at a concentration of 5 mg/mL as a matrix was dissolved in acetonitrile (ACN=Acetonitrile) at a concentration of 50%, and 0.5 uL of this solution was collected, overlaid on the sample on the sample plate, and air-dried to prepare a measurement sample. For this measurement sample, MS/MS analysis was performed in negative ion mode using a mass spectrometer. As the mass spectrometer, MALDI-QIT-TOFMS equipped with a MALDI ion source, a three-dimensional ion trap, and a time-of-flight mass spectrometer, specifically, AXIMA-Resonance (registered trademark) (manufactured by Shimadzu Corporation/Kratos) was used.

Figure 2:
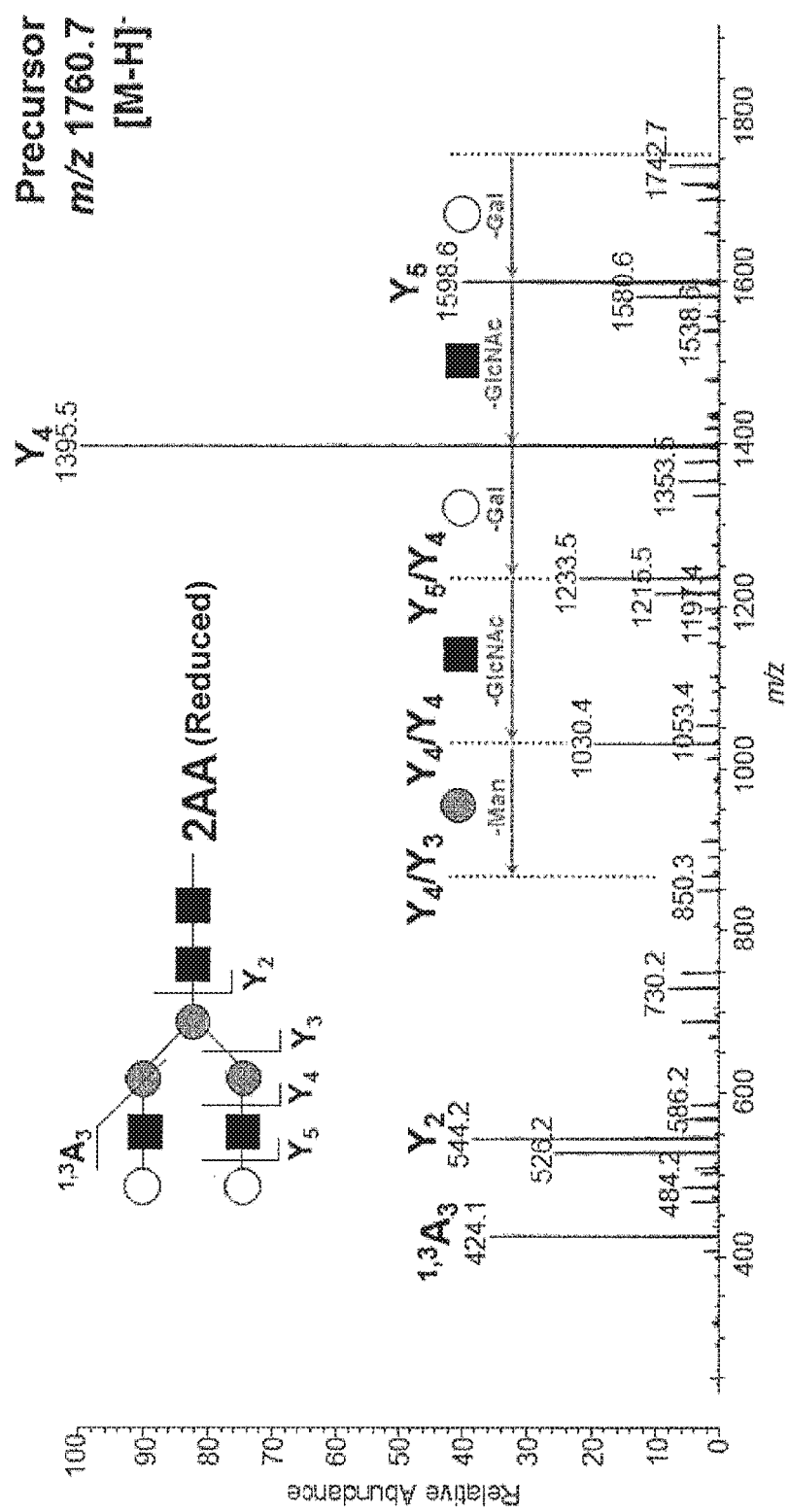
FIG. 2 is a diagram showing an example of MS/MS spectra obtained by MS/MS analysis of biantennary glycans which are 2AA labeled forms (reduced) in negative ion mode.

MS/MS spectra acquired by the above analysis are shown in FIG. 2. FIG. 2 shows a result of MS/MS analysis performed using singly deprotonated ([M—H]$^-$) ions detected at m/z 1760.7 as precursor ions. As can be seen from FIG. 2, most of detected peaks are generated by cleavage of glycosyl bond between monosaccharides, and are y-series ion peaks in which a monosaccharide residue is desorbed in order from a non-reducing terminal of the glycan (a left terminal of the glycan structure shown in FIG. 2). In this case, little or no peaks derived from branched structure-specific product ions, such as D ions and E ions, or peaks derived from cross-ring cleavage of GlcNAc are detected. Therefore, although it is possible to estimate monosaccharides constituting the glycans from the MS/MS spectra, it is very difficult to analyze the branched structure of glycans, Experimental Example 1 Based on Glycan Analysis Method of This Embodiment As a sample, unlabeled NA2 glycan manufactured by SIGMA-ARDRICH, USA was used. A chemical formula of this glycan is the same as that in Comparative Example 1, This glycan was dissolved in a liquid matrix containing 2AA as an acidic group-containing organic substance which is also a labeling agent, and heated to accelerate a reaction between the glycan and 2AA, so that a labeled form of the glycan was formed. More specifically, 5 μL of a tetramethylguanidine (TMG=1,1,3,3,-tetramethylguanidine) stock solution was added to and dissolved in 45 μL of a 2AA solution at 1 M concentration, and 5 μL of this solution was collected and diluted with 45 μL of 50% ACN, then used as a matrix solution (liquid matrix). 0.5 uL of this matrix solution and 1 uL of the sample solution were mixed on a MALDI sample plate (μFocus MALDI plate manufactured by Hudson Surface Technology) and heated on a heat block together with the plate at a temperature of 75° C. for 90 minutes. Although 2AA binds to a reducing terminal of glycan by labeling with 2AA as a labeling agent, reduction is not performed since no reducing agent is used.

Figure 3:
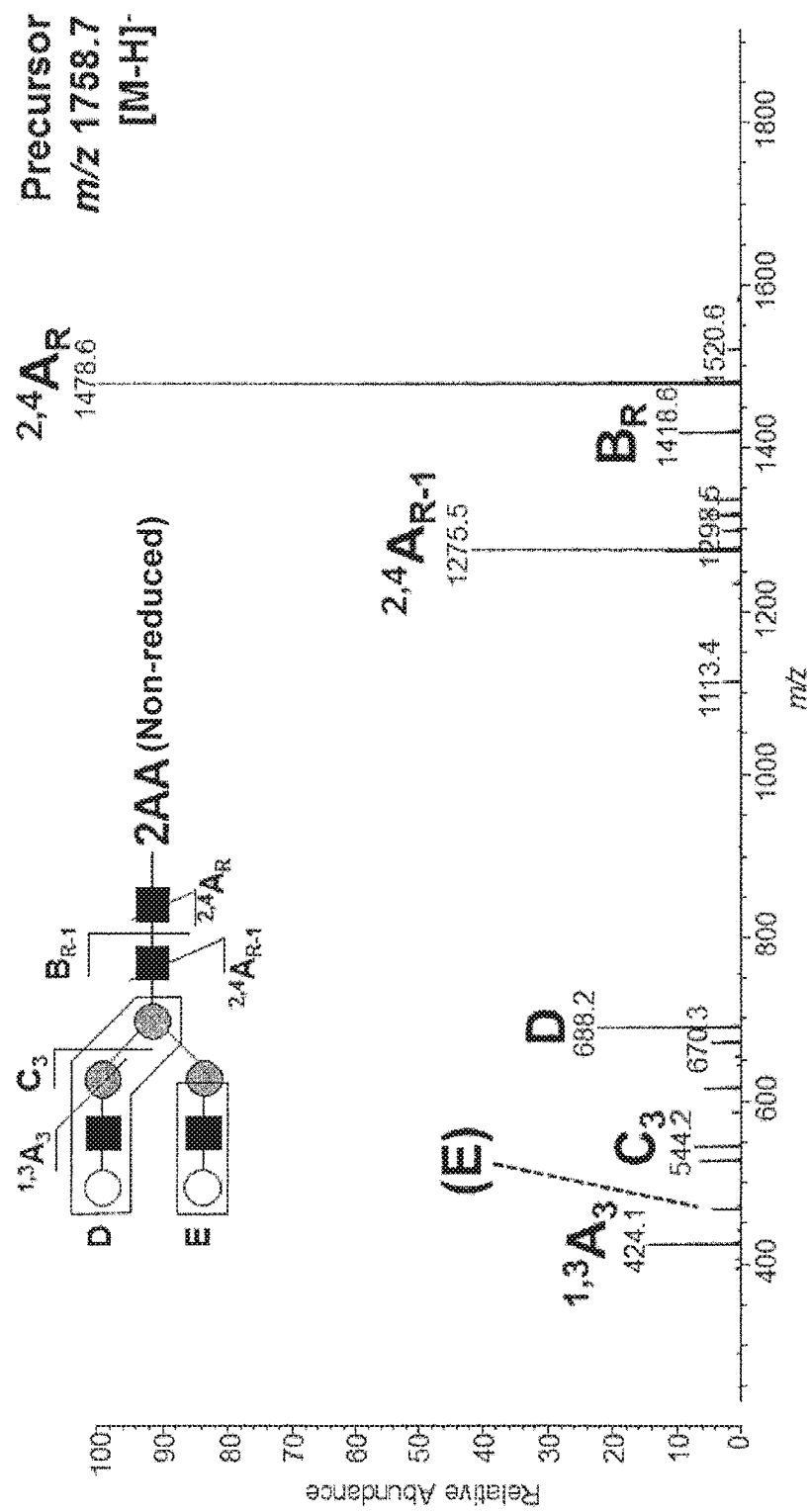
FIG. 3 is a diagram showing an example of MS/MS spectra obtained by MS/MS analysis of biantennary glycans which are 2AA labeled forms (not reduced) in negative ion mode.

The measurement sample us prepared was subjected to MS/MS analysis in negative ion mode using MALDI-QIT-TOFMS in the same manner as that described in Comparative Example 1. MS/MS spectra obtained by this analysis are shown in FIG. 3. FIG. 3 shows a result of MS/MS analysis performed using deprotonated ([M—H]$^-$) ions detected at m/z 1758.7 as precursor ions. Here, since reduction is not performed after labeling as described above, the mass-to-charge ratio of the precursor ions is 2 Da lower than that of Comparative Example 1, but substantially the same as the precursor ions in Comparative Example 1.

As can be seen from FIG. 3, unlike the MS/MS spectra of Comparative Example 1 shown in FIG. 2, peaks derived from D ions and E ions containing information on branched structure are clearly observed. Also, peaks observed in a high mass-to-charge ratio region with m/z=1200 or more are A ions due to cross-ring cleavage (A series) of a GlcNAc residue located on the reducing terminal side of the glycan, and it is possible to estimate a position of fucose from mass difference between the precursor ion and these peaks. Based on the mass-to-charge ratio of each ion, the structure of an entirety of glycan including the branched structure can be easily estimated.

Thus, it can be said that the fact that product ions containing a partial structure on the non-reducing terminal side, such as D ions, E ions, and A ions, are obtained even in a case where negative charges are locally present in the glycan structure like labeling with 2AA is completely unexpected from conventional knowledge.

The chemical reaction for obtaining the non-reduced 2AA labeled form may be performed not on the sample plate but in a container such as a tube. In addition, as is often done with general labeling, a purification step may be provided for removing excess reagent (labeling agent) and the like before executing mass spectrometry.

Comparative Example 2

Figure 4:
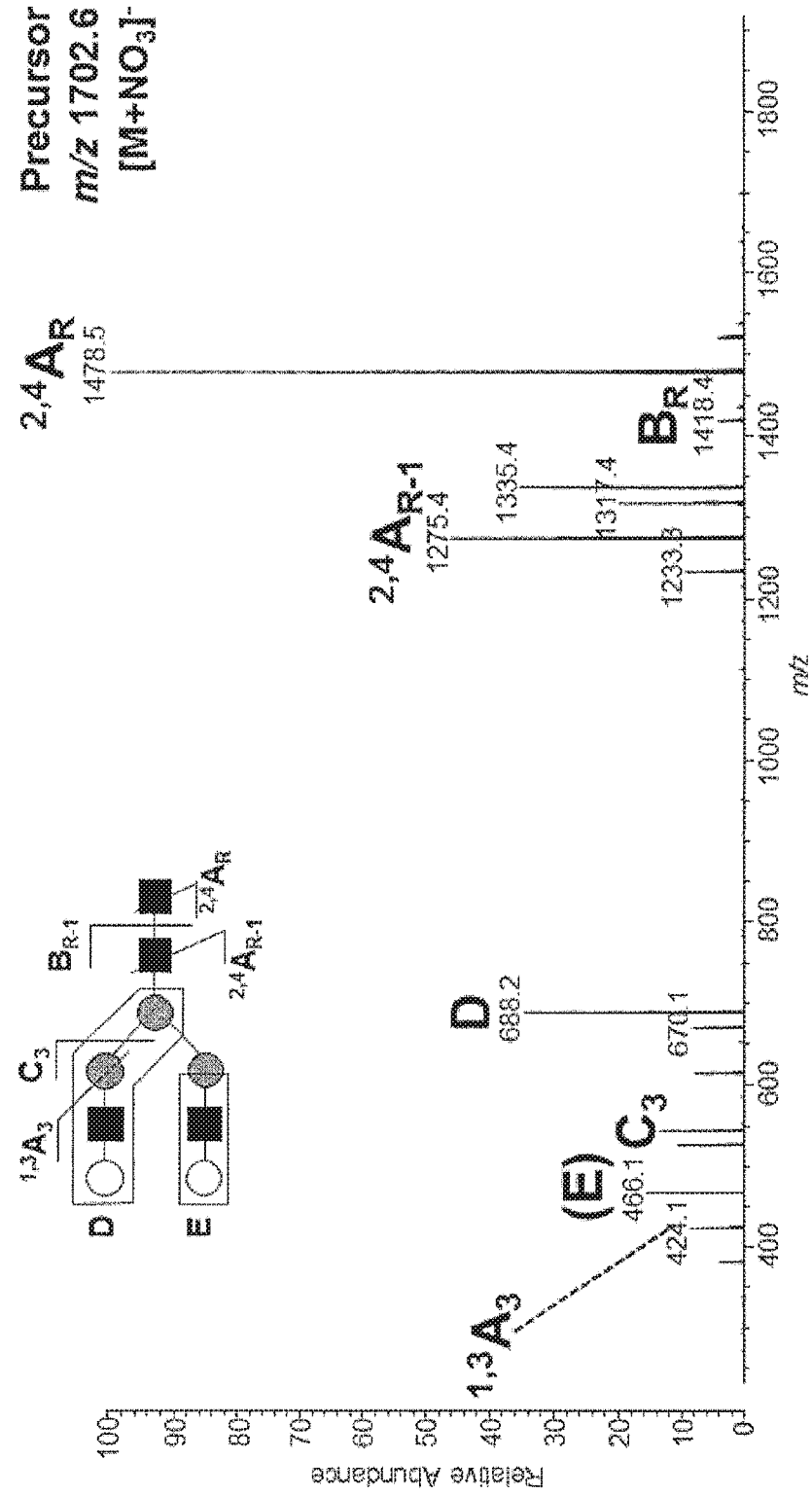
FIG. 4 is a diagram showing an example of MS/MS spectra obtained by MS/MS analysis of a sample prepared using a special liquid matrix added with anions in negative ion mode.

Nitrate adduct ions ([M+NO$_3$]$^-$) of the unlabeled NA2 glycan were subjected to MS/MS analysis based on the conventional method described in Patent Literature 1. Specifically. G$_3$CA (1,1,3,3-tetramethylguanidine p-coumarate) was used as a matrix and ammonium nitrate was used as a matrix additive to prepare a measurement sample. MS/MS spectra obtained by this analysis are shown in FIG. 4. FIG. 4 shows a result of MS/MS analysis performed using nitrate adduct ([M+NO$_3$]$^-$) ions detected at m/z 1702.6 as precursor ions. It can be seen that the MS/MS spectra obtained at this time are considerably close to the MS/MS spectra obtained in Experimental Example 1 shown in FIG. 3, and branched structure-specific product ions are observed. In other words, it can be said that in the glycan analysis method according to the foregoing embodiment, it is possible to obtain MS/MS spectra containing branched structural information of the glycans without using a special matrix such as that described in Comparative Example 2.

Experimental Example 2

Figure 5:
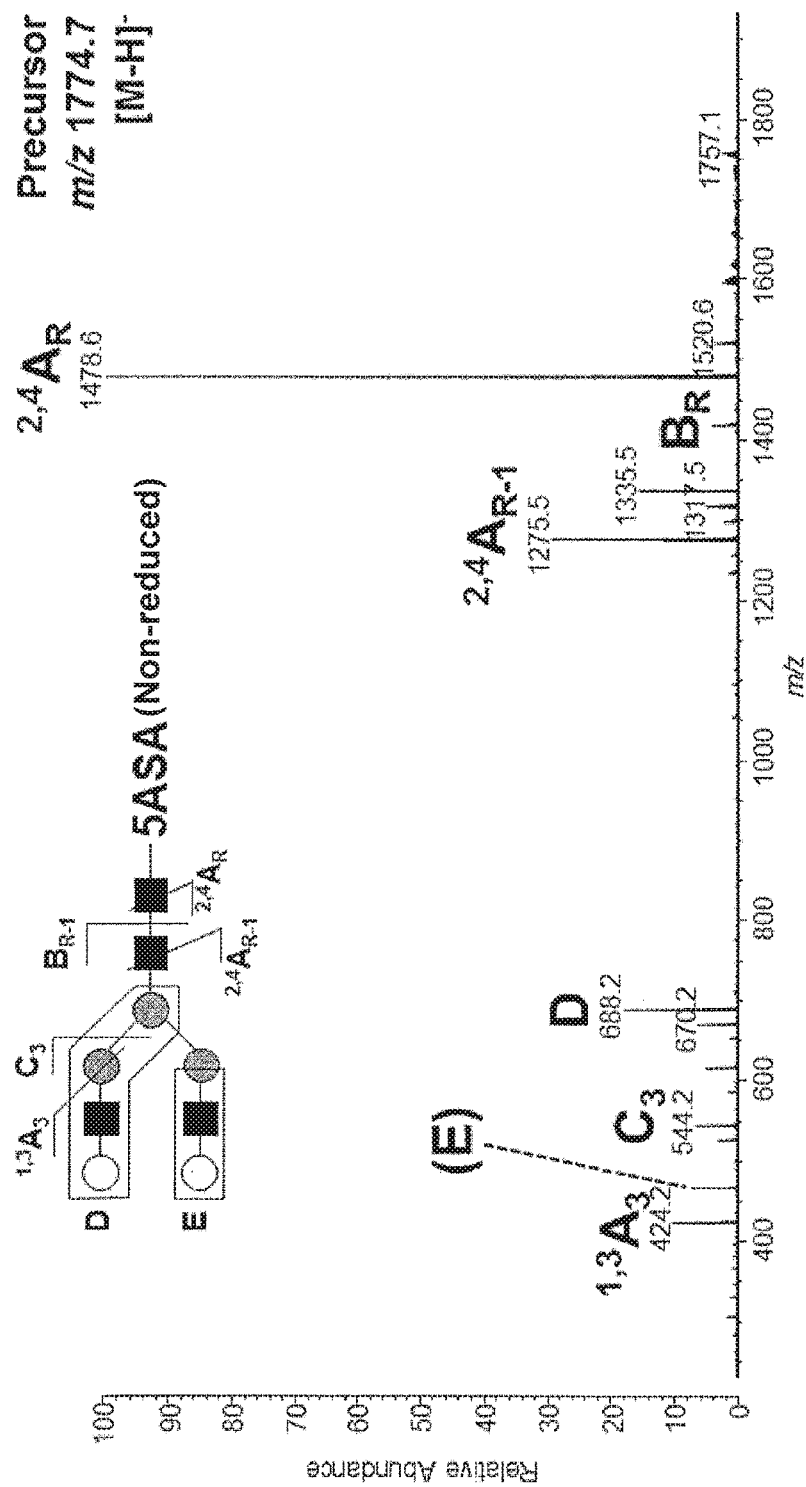
FIG. 5 is a diagram showing an example of MS/MS spectra obtained by MS/MS analysis of biantennary glycans which are 5ASA labeled forms (not reduced) in negative ion mode.

A measurement sample was prepared based on exactly the same procedure as that described in Experimental Example 1 except that 5-aminosalicylic acid (5ASA) was used instead of 2AA for labeling glycans, and MS/MS analysis was performed in negative ion mode. MS/MS spectra obtained by this analysis are shown in FIG. 5. FIG. 5 shows a result of MS/MS analysis performed using deprotonated ([M—H]$^-$) ions detected at m/z 1774.7 as precursor ions.

Peaks almost the same as those of Experimental Example 1, that is, peaks derived from D ions, E ions, and A ions due to cross-ring cleavage of GlcNAc residue in the same mass-to-charge ratio as the MS/MS spectra according to Experimental Example 1 have been observed. From this, it is understood that the glycan analysis method according to the present invention can obtain MS/MS spectra reflecting the same branched structural information irrespective of a chemical structure of the labeling agent as long as the glycans are the same.

The knowledge obtained in Experimental Example 2 is convenient in structural analysis of glycans. That is, when patterns of MS/MS spectra for samples labeled with different labeling agents are nearly the same, it can be concluded that they are the same glycans. Therefore, for example, when MS/MS spectra acquired for various glycans are stored in a database using a certain labeling agent, it is possible to identify unknown glycans prepared using another labeling agent, by collating MS/MS spectra obtained for the unknown glycans with the database. Thus, when restriction on the labeling agent that can be used in identifying glycans is relaxed, an analyst can prepare a sample using his/her own appropriate labeling agent.

It should be noted that the foregoing embodiment is merely an example of the present invention, and any change, modification or addition appropriately made within the spirit of the present invention will evidently fall within the scope of claims of the present patent application.

For example, not only the labeling agents used in the experimental examples, but also other labeling agents having a carboxyl group, a phosphoric acid group, a sulfuric acid group, or the like, such as 2-aminobenzenesulfonic acid, 2-amino-1-naphthalenesulfonic acid, and 4-aminobenzylphosphonic acid may be used in non-reduction. In addition, NHS esters such as "79636 Sigma Atto 590 NHS ester", "72464 Sigma Atto 565 NHS ester", "F9551 Sigma-Aldrich", "73494 Sigma Dy-560 NHS ester", and "55536 Sigma Fluorescent Red Mega 480 NHS ester" exemplified above may be used.

In addition, although the foregoing embodiment is based on the premise that mass spectrometry is performed using a MALDI mass spectrometer, the glycan analysis method according to the present invention is applicable to mass spectrometry using a mass spectrometer by another ionization method performing MS/MS analysis using deprotonated forms (multiply deprotonated form) as precursor ions. That is, the glycan analysis method according to the present invention is applicable to mass spectrometry using an ionization method capable of negative ionization by so-called soft ionization method, for example. ESI method or the like.

The invention claimed is:

1. A glycan analysis method for analyzing a structure of glycan using mass spectrometry, the glycan analysis method comprising:
    a) a sample preparation step of preparing a sample by labeling glycan to be analyzed without reduction, using an acidic labeling agent having at least one site stably presenting a negative charge in a molecule with the acid labeling agent bound to the glycan; and
    b) an analysis execution step of subjecting the sample to MS/MS analysis in negative ion mode, where a deprotonated ion of the glycan labeled in step a is used as a precursor ion;
    c) a detecting step of detecting a product ion of D ion or E ion which reflects a branched structure of the glycan from a result of the MS/MS analysis; and
    d) an estimating step of estimating a structure of the glycan based on step c,
    wherein the site that stably presents a negative charge in the acidic labeling agent is a carboxy group.

2. The glycan analysis method according to claim 1, wherein
    the labeling agent has one site that stably presents a negative charge in a molecule.

3. The glycan analysis method according to claim 1, wherein
    the labeling agent has an amino group, a hydrazide group, an aminooxy group, or a corresponding basic functional group, and binds to a reducing terminal of the glycan.

4. The glycan analysis method according to claim 1, wherein
    the labeling agent reacts with an amino group of a glycosylamine structure in the glycan.

5. The glycan analysis method according to claim 1, wherein
    the analysis execution step executes MS/MS analysis using a deprotonated form of the glycan as a precursor ion.

6. The glycan analysis method according to claim 2, wherein
    the analysis execution step executes MS/MS analysis using a deprotonated form of the glycan as a precursor ion.

7. The glycan analysis method according to claim 3, wherein
    the analysis execution step executes MS/MS analysis using a deprotonated form of the glycan as a precursor ion.

8. The glycan analysis method according to claim 4, wherein
    the analysis execution step executes MS/MS analysis using a deprotonated form of the glycan as a precursor ion.

9. The glycan analysis method according to claim 1, wherein
    the acidic labeling agent has only one site capable of stably presenting the negative charge in the molecule.

* * * * *